United States Patent
Gorschboth et al.

(10) Patent No.: US 8,717,547 B2
(45) Date of Patent: May 6, 2014

(54) PRODUCTION PROCESS FOR AN INTERFACE UNIT AND A GROUP OF SUCH INTERFACE UNITS

(75) Inventors: Claudia Gorschboth, Nürnberg (DE); Jing Li, Erlangen (DE); Klaus Vogler, Eschenau (DE); Olaf Kittelmann, Berlin (DE); Thomas Deisinger, Zirndorf (DE); Gerhard Robl, Stein (DE)

(73) Assignee: Alcon Research, Ltd, Fort Worth, TX (US)

( * ) Notice: Subject to any disclaimer, the term of this patent is extended or adjusted under 35 U.S.C. 154(b) by 694 days.

(21) Appl. No.: 12/894,305

(22) Filed: Sep. 30, 2010

(65) Prior Publication Data

US 2012/0080617 A1 Apr. 5, 2012

(51) Int. Cl.
 *G01C 3/08* (2006.01)
(52) U.S. Cl.
 USPC .......... 356/4.09; 356/3.01; 356/4.01; 356/4.1
(58) Field of Classification Search
 USPC ............. 356/3.01–3.15, 4.01–4.1, 5.01–5.15, 356/6–22, 28, 28.5, 139.01–139.1; 359/665
 See application file for complete search history.

(56) References Cited

U.S. PATENT DOCUMENTS

| | | | |
|---|---|---|---|
| 6,992,765 B2 | 1/2006 | Horvath et al. | |
| 2005/0201221 A1 | 9/2005 | Maeda et al. | |
| 2006/0114469 A1 | 6/2006 | Horvath et al. | |
| 2006/0274425 A1* | 12/2006 | Kuiper et al. | 359/665 |
| 2008/0062796 A1* | 3/2008 | Bates et al. | 365/216 |

* cited by examiner

*Primary Examiner* — Luke Ratcliffe

(57) ABSTRACT

A process for producing an interface unit and also a group of such interface units are specified. The interface unit exhibits a first reference surface for beaming in radiation, a second reference surface for emitting the radiation, and an axis extending in the direction from the first to the second reference surface. The production process comprises the steps of setting an optical path length of the interface unit between the first and second reference surfaces along the axis and the fixing of the set optical path length of the interface unit. The optical path length of the interface unit is set in such a way that radiation of a defined numerical aperture beamed in at the first reference surface exhibits a focus location that is predetermined with respect to the second reference surface in the direction of the axis. A precise and uniform focus location with respect to the second reference surface is obtained.

16 Claims, 6 Drawing Sheets

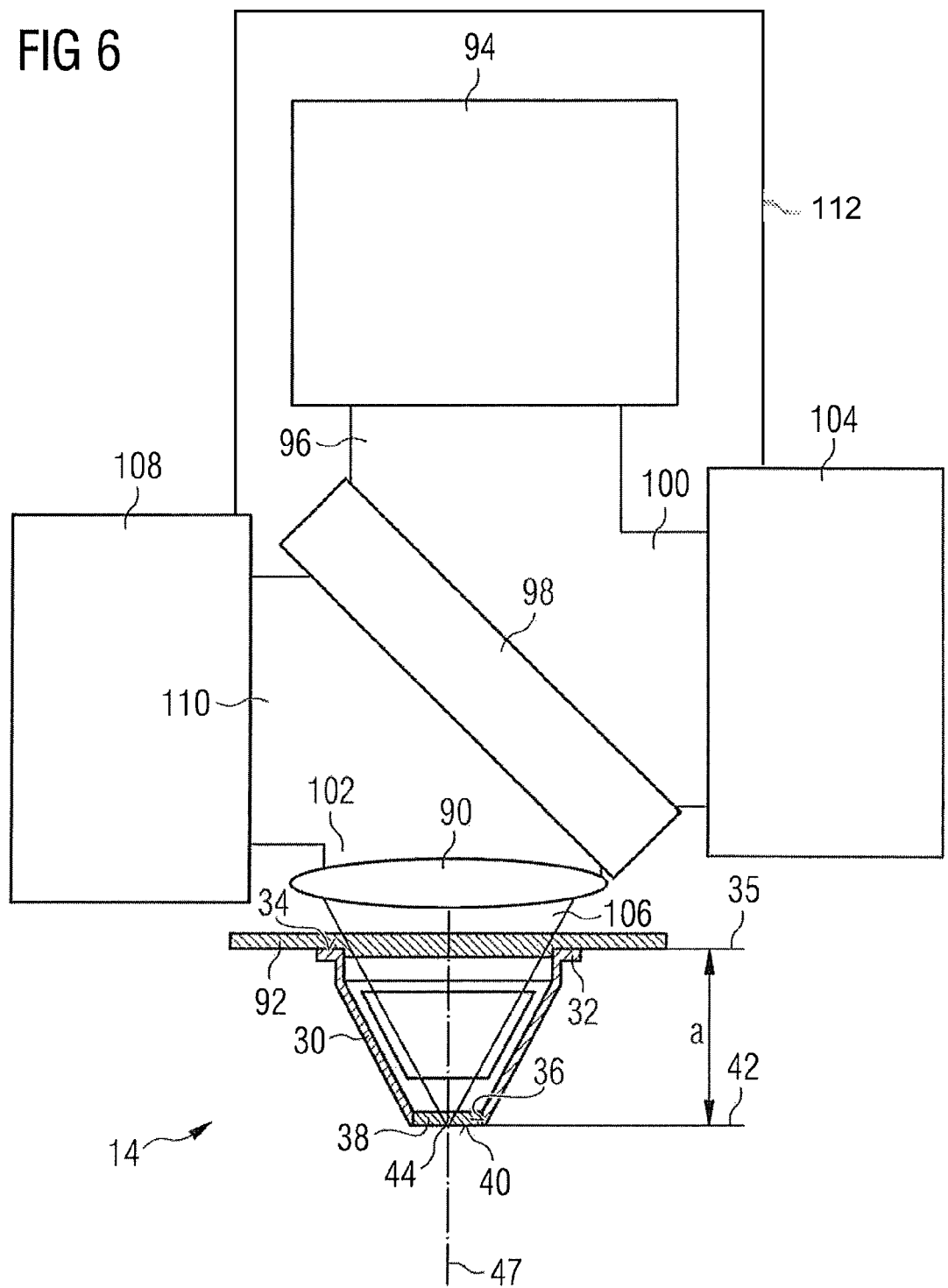

PRODUCTION PROCESS FOR AN INTERFACE UNIT AND A GROUP OF SUCH INTERFACE UNITS

The invention relates to interface units for establishing the relative position between a radiation-source and an object to be irradiated. In particular, the invention relates to a production process for interface units of such a type and to a group of such interface units. The interface units may also be designated as applicators or adapters. To the extent that they are employed in conjunction with radiation-sources for the treatment/machining of human tissue, they can accordingly be designated as patient adapters.

BACKGROUND OF THE INVENTION

There are various forms of treatment that act by means of radiation on a material to be machined. For instance, ultraviolet radiation can trigger a local crosslinking reaction after injection of a photosensitiser. For precise incisions, an accurate localisation of the beam focus of a laser radiation provided by the radiation-source at the desired position of the incision is also required. For this purpose the use of interface units has proved useful, by means of which the object to be irradiated is capable of being positioned with respect to a laser cutting device including the radiation-source.

The materials that are capable of being machined with the laser cutting device may, in principle, be of any nature. They may be dead matter or living (biological) material. An exemplary and by no means limiting field of application of the interface units under consideration here lies in laser-surgical ophthalmology, in which incisions (e.g. individual incisions or complex incision figures) are to be generated in the cornea or in other tissue parts of the human eye by means of focused laser radiation. This field includes, for example, fs LASIK (femtosecond laser in-situ keratomileusis), in which a small disc generally designated in specialist circles by the English term 'flap' is cut out of the anterior region of the cornea by means of ultra-short-pulse laser radiation. The pulse durations that are used customarily are of the order of magnitude of femtoseconds—hence the name fs LASIK. The pulses are focused beneath the anterior surface of the cornea in the interior of the tissue. By positioning the focal points in a desired incision surface, as a result the flap is cut out of the cornea. The flap remains connected to the cornea at a peripheral point and is folded aside for a subsequent ablation (resection of tissue by means of laser radiation) of underlying corneal tissue. After implementation of the ablation, the flap is folded back, and a relatively rapid healing takes place, with the corneal surface remaining largely intact.

It will be understood that the interface units under consideration here may also find application in any other treatment techniques that require generation of an incision in corneal or other ocular tissue. It will be understood, furthermore, that the interface units under consideration within the scope of the invention may also come into operation in other applications that serve for the machining of other forms of biological tissue and even for the machining of dead matter with radiation, above all laser radiation.

In the case of medical applications, particularly in ophthalmology, for reasons of process engineering and hygiene it is additionally necessary that the interface units are sterile articles which are employed anew for each intervention or even for each incision. At the same time, especially in the case of eye operations, particularly stringent demands have to be made of the cutting precision. For a high degree of cutting precision, in addition to an application-dependent form of the beam focus (in shape and size) a high degree of positioning accuracy of the beam focus in the target material is crucial. In the case of eye treatments, for example, a cutting precision of at most a few micrometres, preferably less than 5 μm, is striven for. Ideally, the tissue incision should be able to be placed with an inaccuracy of no more than 1 μm or 2 μm.

For the precision in the depth of incision that is being striven for, a high manufacturing accuracy of the interface units is required. Particularly in ophthalmology, the disposable character and the resulting necessity to provide the interface units in large numbers represent a great challenge for the achievement of the low manufacturing tolerances that are needed. An attempt may be made to predetermine the geometrical dimensions of the interface units. Since the geometrical manufacturing tolerances of the interface units then enter directly into the inaccuracy of the depth of the incision in the tissue, an accurate reproducibility from piece to piece with respect to these geometrical dimensions has to be guaranteed in the course of production of the interface units. For this purpose, on the basis of a reference interface unit a requisite distance between a reference surface facing towards the laser cutting device and a reference surface facing towards the tissue to be treated may, for example, be predetermined and be put into practice uniformly in the production process within the bounds of the manufacturing tolerance.

BRIEF SUMMARY OF THE INVENTION

It is an object of the invention to specify a production process for interface units, so that deviations in the depth of focus, with or even without a further increased manufacturing precision of the geometrical dimensions, are capable of being diminished.

This object is achieved by a process for producing an interface unit with a first reference surface for beaming in radiation, with a second reference surface for emitting the radiation, and with an axis extending in the direction from the first to the second reference surface. The process comprises the steps of setting an optical path length of the interface unit between the first and the second reference surfaces along an axis, and the fixing of the set optical path length. The optical path length of the interface unit is set in such a way that radiation of a defined numerical aperture which is beamed in at the first reference surface exhibits a focus location which is predetermined with respect to the second reference surface in the direction of the axis.

By piecewise setting (adjustment) of the optical path length of the interface unit, in particular in the case of geometrical dimensions of the interface unit varying from piece to piece, the production process enables a predetermined focus location with respect to the second reference surface to be obtained with the necessary accuracy largely independently of geometrical tolerances. With the subsequent fixing of the set optical path length, the interface unit is capable of being produced uniformly with regard to the focus location provided and can be employed directly on a laser cutting device without further adjustment.

The optical path length of the interface unit may have been determined by means of media of differing optical densities that are transparent to the radiation between the first and second reference surfaces. The optical path length can be set by changing at least one of the optical densities. Alternatively or in supplement, by setting—in particular, displacing in the direction of the axis—at least one boundary surface of the media (e.g. a boundary surface between two media or an outer medium boundary surface of the interface unit), the optical path length of the interface unit between the first and the second reference surfaces along the axis can be set. In particular, the optical path length of the interface unit can be set by rearranging the first and second reference surfaces relative to one another in the direction of the axis. For this purpose, the second reference surface may be a boundary surface of one of the media that are transparent to the radiation. By fixing (the relative locations of) the boundary surfaces relative to one another, the optical path length can also be fixed.

The second reference surface may, for example, be constituted by a surface of a contact element that is substantially transparent to the radiation. This surface may be curved or plane. In the case of a design with a plane surface, let the contact element be designated here as an applanation plate, since it is then suitable for levelling soft material for irradiation (for instance, corneal tissue). In particular, the second reference surface may be a surface of a plane-parallel applanation plate.

For the purpose of fixing the set optical path length of the interface unit the applanation plate is advantageously adhesion-bonded to a support. In comparison with an alternative fixing by wedging or/and press fit, by means of adhesion bonding a maladjustment of the set optical path length of the interface unit by reason of material stresses can be avoided. The adhesion bonding may, for example, be triggered or accelerated by using a UV-sensitive adhesive and UV irradiation.

The process may further include, preferably prior to the setting, a registering of the optical path length of a medium of the interface unit, in particular of an applanation plate, by means of a measuring radiation along the axis. In this configuration only a segment of the optical path length between the two reference surfaces is gauged, this segment expediently being defined by boundary surfaces of one or more (but not all) of the optical media of the interface unit. Alternatively or in addition, by means of the (or an additional) measuring radiation the entire optical path length of the interface unit between the first and second reference surfaces can be registered. For the purpose of controlling an actuator rearranging the first and second reference surfaces relative to one another in the direction of the axis, an actuating variable can be ascertained on the basis of the registered optical path length (or lengths). By virtue of a contactless registering by means of the measuring radiation, the optical path length of the at least one medium and/or of the interface unit overall can be monitored advantageously not only during the setting but also during the fixing.

The optical path length can be registered by means of interferometry, preferably by optical low-coherence reflectometry (OLCR). Interferometry permits an extremely precise registering of the optical path length corresponding to a wavelength of the measuring radiation employed, in which connection the low coherence does not make too stringent demands of a radiation-source of the measuring radiation.

For the purpose of registering the optical path length (or lengths) by means of the measuring radiation that is beamed in, a focal beam may be beamed in (in relation to which the radiation provided for the purpose of machining exhibits the defined numerical aperture). In this case an accurate positioning (irrelevant for the later focus location in the course of the treatment) of the interface unit with respect to the radiation-source of the measuring radiation is not necessary.

The ascertainment of the actuating variable may include a calculation of a geometrical length of the interface unit between the first and second reference surfaces along the axis on the basis of the registered optical path length (or lengths) and the predetermined focus location. The actuator is preferably designed to set the calculated geometrical length (directly). An iterative ascertainment of the actuating variable with repeated registering and/or calculating for the purpose of correcting the calculated length may, however, equally be possible.

As an alternative or in supplement to the metrological registering of an optical path length, a measuring radiation with the defined numerical aperture may be beamed in at the first reference surface of the interface unit. A signal of the measuring radiation can be registered after at least a single transit through the interface unit. The first and second reference surfaces can be rearranged relative to one another in the direction of the axis in a manner depending on the registered signal, in particular in a manner depending on a deviation between the registered signal and a reference signal. By means of a rearranging contrary to the deviation, a reference-point (of a controller, of an actuator or of an actuating variable) can be dispensed with.

The registered signal may, for example, characterise an actual wavefront, registered by an analytical detector, of the measuring radiation reflected on the second reference surface. The measuring radiation may, prior to the beaming into the interface unit, pass through an optical system which, for example, is designed to project an afocal measuring radiation into the focal measuring radiation of the defined numerical aperture, and prior to the analysis may pass through the optical system in the opposite direction.

A reference radiation may be coupled out of the measuring radiation expediently prior to reaching the first reference surface and preferably upstream of the aforementioned projecting optical system. The reference signal may characterise an actual wavefront of the measuring radiation registered by means of a reference detector. By comparison with the actual wavefront registered in the analytical detector, even in the case of non-ideal measuring radiation, i.e. deviating from a plane wave, an accurate adjustment is possible. To the extent that the reference radiation is uninfluenced by the interface unit, given insufficient (temporal) stability of the measuring radiation that is beamed in, the nominal wavefront can be registered and stored once or at relatively long time-intervals. Also, the analytical detector may serve at the same time as reference detector by means of an appropriate arrangement.

A splitting mirror for coupling out both the reference radiation and the reflected measuring radiation is preferably employed. Accordingly, the reflected measuring radiation and the reference radiation can be detected in a compact structural design. Furthermore, through the use of a reflector in the reference beam the reference detector may be dispensed with and/or the rearranging in a manner depending on the actual wavefront may be supplemented by a preferably interferometric registering of an optical path length of the interface unit (entire path length or only a fraction).

The invention further provides a group of interface units which each include a first reference surface and a second reference surface. The first reference surface serves for positioning the interface unit with respect to a radiation-source with radiation of an aperture defined uniformly for the group. The second reference surface is spaced from the first reference surface by a geometrical length in the direction of the axis of the interface unit. The second reference surface serves for positioning an object for irradiation with respect to the interface unit and for emitting the radiation. Within the group, a variability of a focus location of the radiation in the direction of the axis with respect to the second reference surface is smaller than a variability of the geometrical length. The variability may be an absolute variability or a relative variability relative to a mean value or nominal value. A variance, for example, may serve as a measure of the variability within the group.

The interface units may each include a contact element, transparent to the radiation, with a contact surface, forming the second reference surface, for abutment against an object for irradiation. They may, in addition, include a support for the contact element, forming the first reference surface and exhibiting one or more coupling-abutment structures for coupling to a component of the radiation-source, in particular to a focusing objective. The support may exhibit a retaining body widening in the manner of a funnel, at the narrow end of which the contact element is arranged.

The contact surface may be plane or curved (e.g. concave).

In a preferred configuration the interface units each exhibit a total of two media, transparent to the radiation and of differing optical densities, between the first and second reference surfaces, one of the media being air and the other medium being constituted by the contact element.

The group may, for example, be a batch from a production run of the interface units. As a result, a simple interchange of the interface units, in particular as disposable articles, is possible. An elaborate readjusting, which is delaying in the course of an operation, of the radiation-source or of the positioning of the interface unit with respect to the radiations-source can consequently be dispensed with.

BRIEF DESCRIPTION OF THE DRAWINGS

The invention will be elucidated further in the following on the basis of the appended drawings. Represented are:

FIGS. 4 to 6: schematically, apparatuses for various adjusting methods for application in the course of production of the interface unit shown in FIG. 1.

DETAILED DESCRIPTION OF PREFERRED EMBODIMENTS

Figure 1:
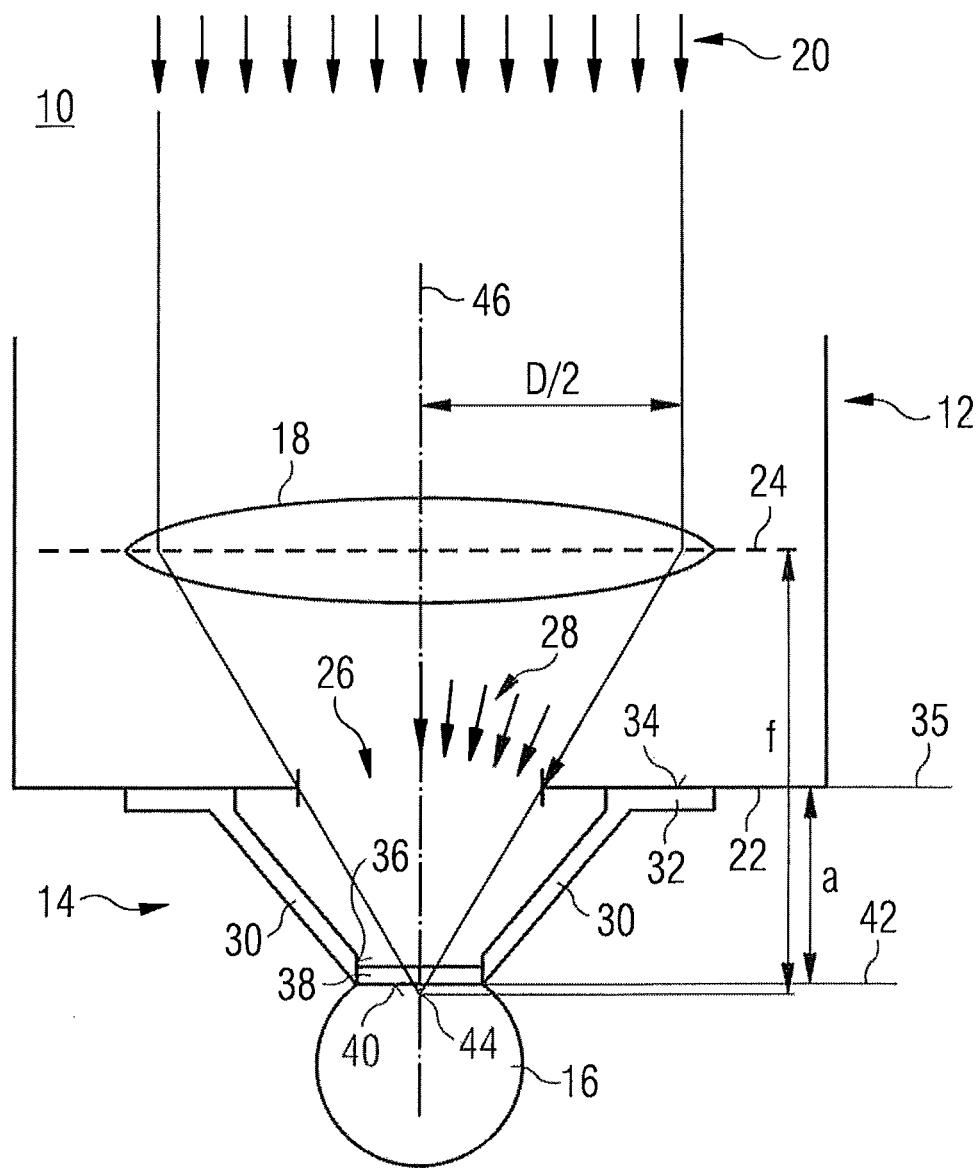
FIG. 1: schematically, an arrangement of an exemplary interface unit for coupling an object to be machined to a laser cutting device serving as radiation-source via the interface unit.

FIG. 1 shows a laser cutting device denoted generally by 10 with a radiation-source 12 and with an interface unit 14 for cutting tissue in an eye 16. The radiation-source 12 includes an optical system 18 with a focal length f for focusing an incident parallel (afocal) ray bundle 20 which a femtosecond laser (not shown) generates. An attachment surface 22 of the radiation-source 12 extends parallel to and at a fixed spacing from a principal plane 24 of the optical system 18, so that the incident parallel ray bundle 20 emerges at an opening 26 in the attachment surface 22 as a convergent (focal) ray bundle 28.

The interface unit 14 includes a conical spacing element (support) 30 with an annular flange 32 at the wide end of the cone. The annular flange 32 forms an outer abutment surface 34 which defines the first reference surface 35 of the interface unit 14. The abutment surface 34 of the interface unit 14 in this particular application abuts the attachment surface 22 of the radiation-source 12 and is, for example, fixed thereto by a bayonet catch (not shown).

At the opposite (tapered) cone end of the spacing element 30 an opening 36 for enclosing a contact element 38 that is transparent to the radiation is provided, here a biplanar applanation plate made of glass or plastic. The contact element 38 exhibits a plane outer surface 40, provided for abutment against the eye 16, as second reference surface 42 of the interface unit 14. The contact element 38 is fixed in the opening 36 with the outer surface 40 parallel to the first reference surface 35. Hence a geometrical spacing a between first reference surface 35 and second reference surface 42 can be specified as a dimension of the interface unit 14.

The eye 16 is brought into abutment with its surface against the outer surface 40 of the contact element 38, for example by reduced pressure or by mechanical pressing. The laser radiation cuts the ocular tissue at a focal point 44 on an optical axis 46 which in this particular application is moved over the treatment surface in accordance with the desired incision figure. The depth of incision in the ocular tissue is determined by a spacing, denoted in the following by c, between second reference surface 42 and focal point 44. In the following, for the purpose of clarity an optical axis 46 perpendicular to the reference surfaces 35, 42 will be assumed.

Figure 2:
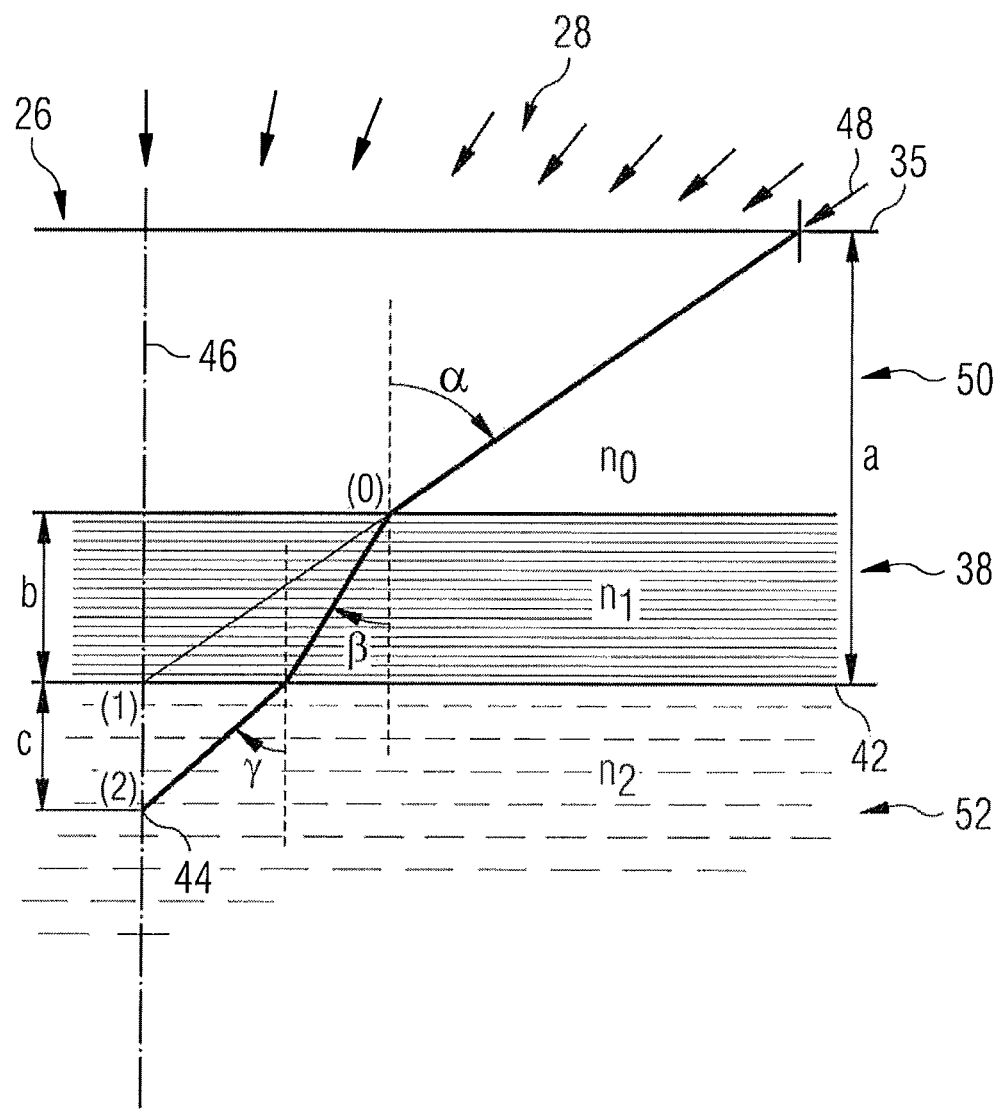
FIG. 2: schematically, a progression of a radiation beamed in with defined numerical aperture through the interface unit and into the object to be machined.

Whereas the focal point 44 in the case of a free propagation (i.e. in the absence of a contact element 38) would be situated at a spacing f from the principal plane 24 corresponding to the focal length of the optical system 18, the depth of focus in the ocular tissue is displaced rearward by the contact element 38. FIG. 2 shows the displacement schematically. The focal ray bundle 28 falls into the interface unit 14 (FIG. 1) through the opening 26 on the first reference surface 35 with a numerical aperture NA that is characteristic of the radiation-source 12.

A marginal ray 48 singled out from the incident focal ray bundle 28 in exemplary manner exhibits an angle $\alpha$ relative to the optical axis 46. The ray 48 passes through, as first optical medium 50, air with a refractive index $n_0$ and impinges at a point (0) on the contact element 38 as second optical medium. Whereas without the contact element 38 the ray 48 would intersect the optical axis 46 in rectilinear manner at a point (1) and hence would define an undisplaced focal point (1) (virtual focal point), by virtue of the higher refractive index $n_1$ a refraction of the ray 48 occurs with an angle $\beta(<\alpha)$ relative to the optical axis 46. After the ray 48 has traversed the contact element 38 with thickness b, the ray 48 passes at an angle $\gamma$ relative to the optical axis 46 into the ocular tissue denoted by 52 as third optical medium with a refractive index $n_2$. The ray 48 intersects the optical axis at a point (2) displaced along the axis by a spacing c in the beam direction. Since all the other rays of the ray bundle 28 also intersect at point (2), this is the rearward-displaced focal point 44. For the spacing c as a function of the thickness b of the contact element 38 and as a function of the angles of refraction $\alpha$, $\beta$, $\gamma$ it holds that:

$$c = [(a_{(1)} - a)\tan\alpha + b(\tan\alpha - \tan\beta)]/\tan\gamma \quad \text{(Eqn. 1)}$$

where $a_{(1)}$ denotes the spacing of the virtual focal point (1) predetermined by the focal length f of the optical system 18 (in the case of an opening 36 not closed by the contact element 38) from the first reference surface 35 (i.e. $a_{(1)}$ is the focal length f minus the spacing between principal plane 24 and first reference surface 35). The geometrical length a is the spacing shown in FIGS. 1 and 2 between the first reference surface 35 and the second reference surface 42.

Consequently, manufacturing tolerances in the geometrical length a between first reference surface 35 and second reference surface 42 of the interface unit 14 and also tolerances in the thickness b of the contact element 38 enter directly into the incision depth c by way of inaccuracy. A deviation $\Delta b$ in the thickness b of the contact element 38 results in an error $\Delta f_b$ in the incision depth c:

$$\Delta f_b = \Delta b \sqrt{n_2^2 - NA^2} \left( \frac{1}{\sqrt{1 - NA^2}} - \frac{1}{\sqrt{n_1^2 - NA^2}} \right) \quad \text{(Eqn. 2)}$$

where the refractive index $n_0$ of the air 50 is assumed to be $n_0$=1. A further error contribution $\Delta f_a$ arises for the incision depth c by virtue of a deviation $\Delta a$ in the length a.

Figure 3:
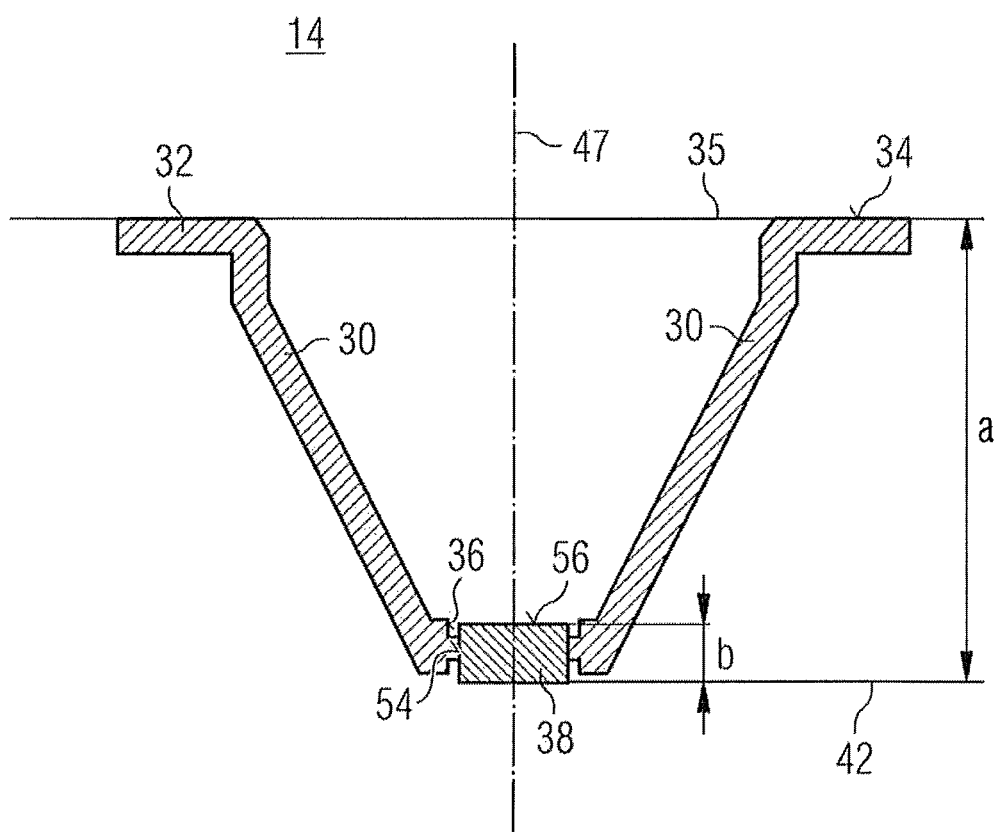
FIG. 3: an axial longitudinal section through the interface unit shown in FIG. 1.

The interface unit 14 shown in FIG. 3 avoids the disadvantages of an inaccurate depth of focus c, in that in the course of production the distance a between the first reference surface 35 and the second reference surface 42 is set as a function of the thickness b actually obtaining in the given case or as a function of an optical thickness $n_1 b$ of the contact element 38.

In FIG. 2 the case $a_{(1)}$=a is shown—i.e. the virtual focal point (1) coincides with the outer surface 40 of the contact element 38. The aim of the production process is to set an optical path length of the interface unit 14 between first reference surface 35 and second reference surface 42 along an axis 47 of the interface unit 14 in such a way that the focal point 44 again coincides with the outer surface 40 (depth of focus c=0). This predetermined focus location serves in the later particular application as 'zero point' for the focus control in the direction of the optical axis 46. Of course, another virtual focal point (1) (with $a_{(1)} \neq a$) may also be assumed, and another focus location (with depth of focus c≠0) may be predetermined for production. The axis 47 of the interface unit 14 is tantamount to a cone axis of the conical spacing element 30 (FIG. 1); the reference surfaces 35, 42 are oriented orthogonally to this (mechanical) axis 47. In the case where the optical axis 46 of the incident focal ray bundle 28 is equally orthogonal to the reference surfaces 35, 42, the axes 46, 47 are collinear.

The opening 36 in the spacing element 30 exhibits, in the exemplary case that is shown, a circumferential enclosing surface 54 (alternatively, several adjacent enclosing surfaces). Independently of the adjustment process, the contact element 38 is adhesion-bonded to the enclosing surface 54 at the set optical path length.

In an embodiment the exact axial thickness b of the contact element 38 is measured as a geometrical spacing of its inner surface 56 and the outer surface 40, and the geometrical length a along the axis 47 is calculated therefrom, for example by solving the above Eqn. 1. In the course of production of the interface unit 14 the contact element 38 is then moved along the optical axis 47 relative to the spacing element 30 until the calculated length a for the measured thickness b given predetermined numerical aperture NA corresponds to the desired depth of focus c.

The above Eqn. 1 is of the linear form $$c = C_0 + C_1^{(1)} a + C_2^{(1)} b \quad \text{(Eqn. 1.1)}$$

where the coefficients $C_0 = a_{(1)} \tan \alpha / \tan \gamma$, $C_1^{(1)} = -\tan \alpha / \tan \gamma$, and $C_2^{(1)} = (\tan \alpha - \tan \beta)/\tan \gamma$ are permanently predetermined by the radiation-source 12, in particular the optical system 18 (FIG. 1). For the purpose of setting the optical path length, instead of predetermining the geometrical variables a and b as nominal variables or registering them as actual variables, the entire optical path length $L_S$ of the interface unit 14 between the first and the second reference surfaces 35, 42

$$L_S = n_0 a + (n_1 - n_0) b \quad \text{(Eqn. 3)}$$

and/or the optical thickness $L_b$ of the contact element 38

$$L_b = n_1 b \quad \text{(Eqn. 4)}$$

can be taken as the basis for the adjustment. Corresponding conditional equations follow from Eqn. 1.1 by inserting Eqns. 3 and 4:

$$c = C_0 + C_1^{(2)} L_S + C_2^{(2)} L_b \quad \text{(Eqn. 1.2)}$$

$$c = C_0 + C_1^{(3)} a + C_2^{(3)} L_b \quad \text{(Eqn. 1.3)}$$

$$c = C_0 + C_1^{(4)} L_S + C_2^{(4)} b \quad \text{(Eqn. 1.4)}$$

$$c = C_0 + C_1^{(5)} a + C_2^{(5)} L_S \quad \text{(Eqn. 1.5)}$$

For example, for the combination of variables ($L_S$, $L_b$) of Eqn. 2 the following hold:

$C_1^{(2)} = C_1^{(1)}/n_0$ and $C_2^{(2)} = C_2^{(1)}/n_1 + C_1^{(1)}(1/n_1 - 1/n_0)$.

Figure 4:
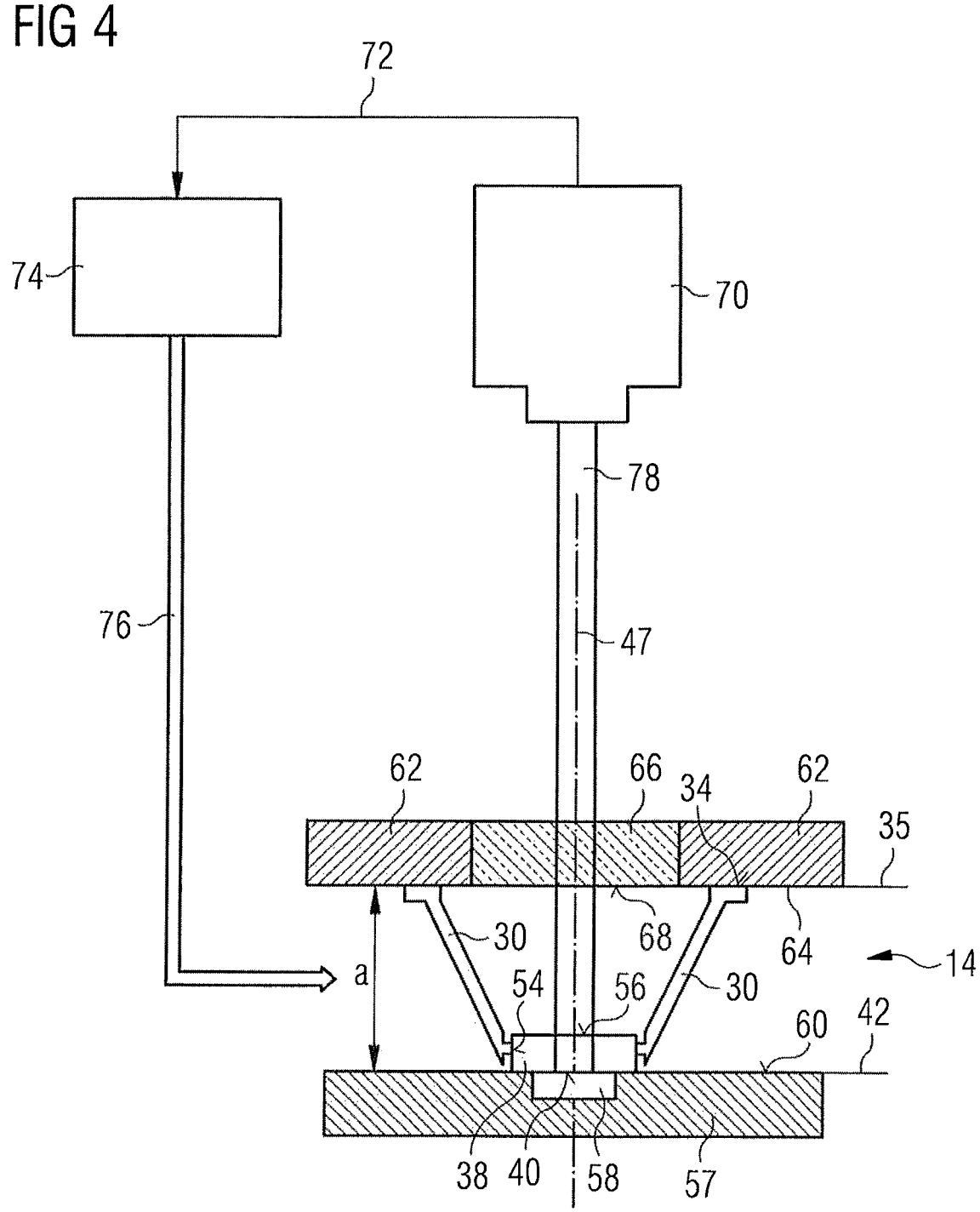

FIG. 4 shows an embodiment of an adjustment apparatus with a bearing table 57 for the contact element 38. The latter protrudes axially beyond the spacer 30 and is supported on the bearing table 57. The contact element 38 is inserted into the spacing element 30 in such a way that although it is held frictionally therein it is still capable of being rearranged axially in relation to the spacing element 30 by means of suitable actuating forces. A definitive fixing is effected by adhesion bonding.

The bearing table exhibits a beam trap constituted by a cavity 58. For the purpose of signal amplification, in an alternative embodiment a reflector surface 60 perpendicular to the axis 47 may have been enclosed. Furthermore, an axially fixed interface-element support 62 is provided, with a positioning surface 64.

A spacing-measuring instrument 70 is capable of sending a measured variable 72 representing the optical thickness $L_b$ along the axis 47 to a control unit 74. The control unit 74 derives from the measured variable 72 an actuating variable 76 which drives an actuator (not shown) which moves the bearing table 57 along the axis 47 relative to the support 62.

The spacing-measuring instrument 70 operates in accordance with the principle of optical low-coherence reflectometry (OLCR). The spacing-measuring instrument 70 generates an afocal laser beam and splits the latter into a reference branch (not shown) and an afocal measuring beam 78. The working wavelength of the spacing-measuring instrument 70 is preferably chosen to be in the vicinity of the wavelength of the radiation of the laser system 10. In the event of a significant difference between the wavelength of the measuring beam 78 and the wavelength of the laser system 10 suitable correction algorithms may be implemented in the control unit 74.

A first reflection arises on the inner surface 56 of the contact element 38. The contact element 38 generates on the outer surface 40 a second reflection corresponding to the axial location of the second reference surface 42. The first and second reflections re-radiated into the spacing-measuring instrument 70 are in each instance caused to interfere therein with the reference branch, whereby the path length of the reference branch is lengthened or shortened in accordance with the interference signal. From the reference-branch lengths for the first reflection and for the second reflection the spacing-measuring instrument 70 determines the optical thickness $L_b$ of the contact element 38 by way of measured variable 72.

During the adjustment the first reference surface 35 of the interface unit 14 is fixed on the positioning surface 64 and remains stationary; the outer surface 40 of the contact element 38 defining the second reference surface 42 rests on a surface 60 of the table 57. As a result, the contact element 38 is capable of being rearranged in the direction of the axis 47 until attaining a spacing a calculated by the control unit 74, for example in accordance with Eqn. 1.3, by way of actuating variable 76 for the measured optical thickness $L_b$.

In a further development of this embodiment for the combination of variables ($L_S$, $L_b$) a reflection plate 66 that is transparent to the laser radiation is enclosed in the interface-element support 62. The reflection plate 66 terminates towards the interface unit 14 with a flat reflection surface 68 flush with the positioning surface 64, so that the reflection plate 66 generates on the reflection surface 68 a third reflection of the measuring beam 78 corresponding to the axial location of the first reference surface 35. By reason of the second and third reflections, the spacing-measuring instrument 70 generates a measured variable 72 representing the optical length $L_S$ between the first reference surface 35 and the second reference surface 42. The control unit 74 calculates, for example in accordance with Eqn. 1.2, a correcting actuating variable 76 from the optical measured variables $L_S$, $L_b$. This has the advantage that an actuator can be employed without absolute length scale for the geometrical length a (and even without length calibration).

Figure 5:
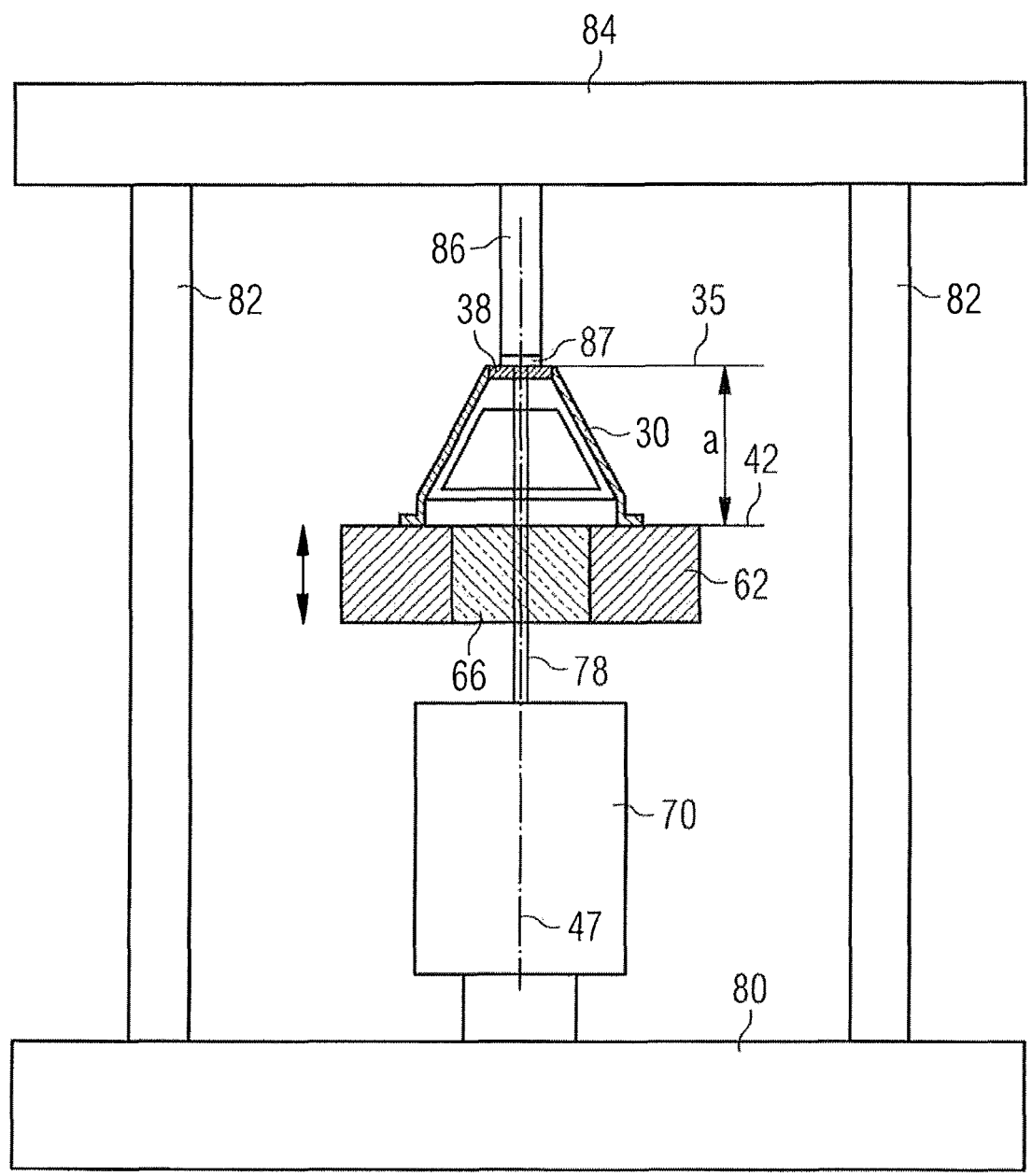

FIG. 5 show an alternative in which the spacing-measuring instrument 70 is immovably connected to a carrier 84 via a base 80 and props 82, so that a receiver 87 fitted at one end of a stamp 86 is fixed with respect to the spacing-measuring instrument 70 while the actuator moves the interface-element support 62, with the reflection plate 66 enclosed therein, along the axis 47. The control of the actuator in a manner depending on the reflections generated on the first reflection surface 35 and on the second reflection surface 42 is as described with reference to FIG. 4.

The stamp 86 and the receiver 87 may, for example, exhibit an axial passageway in which a reduced pressure prevails, in order to aspirate the contact element 38 in such a way that no undesirable curvature of the reflection surfaces is induced. This is, for example, attainable by means of an annular design of the passageway (intake port). In this way, an automatically separable linkage between receiver 87 and contact element 38 is made possible for the adjustment.

In another embodiment (not shown), radiation of numerical aperture NA is beamed in at the first reference surface 35, and the location of the focal point 44 on the axis 47 (in the vicinity of the second reference surface 42) is determined while the contact element 38 is being moved along the axis 47 until the desired depth of focus c has been attained. The location of the focal point is determined by a CMOS sensor or CCD sensor (with its sensor surface at right angles to the axis 47), the position of which along the axis 47 is controlled in such a way that a spot of light registered by the sensor assumes a minimal lateral extent.

FIG. 6 shows an embodiment of an adjustment apparatus which exhibits a focusing optical system 90 (represented by a single collecting lens) which is rigidly connected, in a manner not represented in any detail, to a support 92 for the interface unit 14 to be adjusted. The interface unit 14 is capable of being mounted on the support 92 in such a way that its axis 47 is coaxial with the optical axis of the optical system 90. The adjustment apparatus further exhibits a laser radiation-source 94, the generated laser radiation of which (same wavelength as the laser system 10) impinges as parallel (afocal) ray bundle 96 on a beam-splitter 98 which splits the ray bundle 96 into a reference beam 100 and a measuring beam 102. The reference beam 100 arrives at a reference detector 104 in which a wavefront signal that is representative of the progression of the wavefront of the reference beam 100 is generated. The (still afocal) measuring beam 102 is beamed into the optical system 90 with bundle axis coaxial with the axis 47 of the interface unit 14 and is projected by said optical system onto a focal ray bundle 106, the numerical aperture of which is identical to the numerical aperture of the focused laser radiation provided for the purpose of machining in the later particular application. Instead of a laser radiation-source 94, use may also be made of another radiation-source (preferably of similar mid-wavelength to that of the laser system 10) that generates non-coherent radiation.

The spacing element 30 of the interface unit 14 is firmly connected to the support 92. For this purpose the support 92 exhibits a suitable abutment surface for the annular flange 32 of the spacing element 30. Clamping means which are not represented in any detail may, for example, serve for separable clamping of the spacing element 30 on the support 32.

The contact element 38 is, in turn, already inserted into the opening 36 in the spacing element 30; however, it is not yet fixed therein but is displaceable relative to the spacing element 30 in the direction of the axis 47. A positioning member which is not represented in any detail and which is capable of being rearranged in the axial direction is capable of being brought into separable engagement with the contact element 38, so that by actuation of the positioning member an axial relocation of the contact element 38 relative to the spacing element 30 is possible.

In a manner analogous to the preceding embodiments, also in the embodiment according to FIG. 6 the optical path length of the interface unit 14 between the two reference surfaces 35, 42 is rearranged by relative axial relocation of the contact element 38 in relation to the spacing element 30. The rearrangement is effected in this case so far or for so long until a signal derived from the measuring beam 102 and, concretely, from the transit of the convergent ray bundle 106 through the interface unit 14 satisfies a predetermined condition. In the exemplary case shown in FIG. 6, even though the optical system 90 and the support 92 are fixed and the contact element 38 is capable of being relocated relative to this fixed assembly with the spacing element 30 fixed thereon, it is of course conceivable to fix the contact element 38 axially and to design the assembly consisting of optical system 90 and support 92 to be axially adjustable.

The setting of the interface unit 14 is effected with the proviso to place the focal point 44 along the axis 47 into the second reference surface 42 (i.e. depth of focus c=0). In order to be able to examine this condition, the adjustment apparatus exhibits an analytical detector 108 which analyses the wavefront progression of a ray bundle 110 (reflection beam) reflected on the outer surface 40 of the contact element 38 and coupled out by means of the beam-splitter 98. Given correct axial setting of the contact element 38, the radiation reflected on the outer surface 40 is projected by the optical system 90 into a parallel (afocal) ray bundle, the wavefront progression of which corresponds to that of the reference beam 100. Once the contact element 38 has been axially displaced in relation to this ideal state, the wavefront progression of the reflection beam 110 differs from that of the reference beam 100. The analytical detector 108 or an evaluating unit incorporated therein or connected thereto compares the reference wavefront signal 112 provided by the reference detector 104 (tantamount to a nominal wavefront) with a wavefront signal ascertained for the reflection beam 110 and characterising the wavefront progression thereof (tantamount to an actual wavefront) and brings about, depending on a deviation between the two wavefront signals, an axial relocation of the contact element 38 relative to the spacing element 30 until this deviation disappears or is minimised in accordance with predetermined thresholds. Given sufficient concordance between the actual wavefront and the nominal wavefront, the contact element 38 is fixed in its set axial position relative to the spacing element 30, preferably again by adhesion bonding.

Insofar as in the case of the above adjustment process a measuring beam of the same numerical aperture as in the intended application is employed, the interface unit 14 can be manufactured with such a geometrical length which guarantees that in the later application the axial position of the focus lies exactly at the desired location relative to the second reference surface 42.

In all the aforementioned embodiments the abutment surface 34 may provide, instead of a circumferential flange 32, a three-point bearing (defining the first reference surface 35). In corresponding manner, the production process is applicable for a curved inner surface 56 or a curved outer surface 40 of the contact element 38. Additionally or in supplement, a transparent correction chamber (not shown) may have been provided in the spacing element 30 for the purpose of receiving a gas. The correction chamber is passed through by the axis 47. By raising or lowering the gas pressure in the correction chamber, the optical density of the correction chamber and hence the optical path length of the interface unit 14 along the axis 47 can be set. The set optical path length can then be fixed by closing the correction chamber.

The production process can be employed for the purpose of manufacturing each interface unit for laser material-machining instruments in which a stable positioning of the machining area is effected via the interface unit. The focus location 44 obtained with the production process is independent of manufacturing tolerances of the geometrical dimensions of the spacing element 30, in particular its length in the direction of the axis 47, and independent of manufacturing tolerances of the optical density $n_1$ and geometrical dimensions of the contact element 38, in particular its thickness b. At the same time, the focus location 44 with respect to the outer surface 40 (and accordingly, for example, an incision depth in the target tissue) can be obtained with an accuracy of a few micrometres, preferably less than 5 μm and in particular about 1 μm. A group of correspondingly produced interface units 14 may exhibit a variability with regard to the geometrical length that exceeds the variability of the depth of focus.

The invention claimed is:

1. A process for producing an interface unit having comprising:
    receiving the interface unit comprising a conical spacing element and a contact element, the conical spacing element having an annular flange that defines a first reference surface for beaming in radiation, the contact element defining a second reference surface for emitting the radiation, the interface unit having an axis extending in the direction from the first to the second reference surface, the conical spacing element having an opening that holds the contact element and allows the contact element to be displaceable along the axis,
    setting an optical path length of the interface unit between the first and second reference surfaces along the axis, so that radiation of a given numerical aperture beamed in at the first reference surface exhibits a focus location that is predetermined with respect to the second reference surface in the direction of the axis, and
    fixing the set optical path length of the interface unit by fixing the contact element in its position along the axis such that the contact element is no longer displaceable along the axis.

2. The process according to claim 1, wherein the optical path length of the interface unit is determined by media that are transparent to the radiation and of differing optical densities between the first and second reference surfaces, and the optical path length of the interface unit is set by at least one of changing one or more of the optical densities and displacing at least one boundary surface of the media in the direction of the axis.

3. The process according to claim 2, wherein the step of displacing includes rearranging the first and second reference surfaces relative to one another.

4. The process according to claim 1, wherein the contact element comprises an applanation member that is transparent to the radiation.

5. The process according to claim 4, wherein the applanation member is a plane-parallel applanation plate.

6. The process according to claim 1, wherein fixing the set optical path length comprises adhesion bonding the contact element to the conical spacing element.

7. The process according to claim 1, further comprising the following steps:
    by means of a measuring radiation along the axis, determining at least one of the optical path length of a medium of the interface unit and the optical path length of the interface unit between the first and second reference surfaces,
    ascertaining an actuating variable for controlling an actuator for rearranging the first and second reference surfaces relative to one another in the direction of the axis on the basis of the determined optical path length.

8. The process of claim 7, wherein the medium is an applanation member of the interface unit.

9. The process according to claim 7, wherein the optical path length is determined by optical low-coherence reflectometry.

10. The process according to claim 7, wherein the measuring radiation beamed in is afocal.

11. The process according to claim 7, wherein the step of ascertaining includes calculating a geometrical length of the interface unit on the basis of the determined optical path length and the predetermined focus location.

12. The process according to claim 1, further comprising the following steps:
    beaming a measuring radiation having the given numerical aperture at the first reference surface into the interface unit,
    detecting a signal of the measuring radiation after at least one transit of the measuring radiation through the interface unit, and
    rearranging the first and second reference surfaces relative to one another in the direction of the axis based on the detected signal.

13. The process of claim 12, wherein the step of rearranging includes rearranging the first and second reference surfaces relative to one another based on a deviation between the detected signal and a reference signal.

14. The process according to claim 12, wherein the detected signal characterises an actual wavefront, detected by means of an analytical detector, of the measuring radiation reflected on the second reference surface.

15. The process according to claim 14, further comprising the following step:
coupling a reference radiation out of the measuring radiation, the reference signal characterising a nominal wavefront of the reference radiation detected by means of a reference detector.

16. The process according to claim 15, wherein a splitting mirror is employed for coupling out both the reference radiation and the reflected measuring radiation.

* * * * *